(12) United States Patent
Noda et al.

(10) Patent No.: US 11,357,455 B2
(45) Date of Patent: Jun. 14, 2022

(54) INFORMATION PROCESSING APPARATUS, RADIATION IMAGING APPARATUS, INFORMATION PROCESSING METHOD, AND STORAGE MEDIUM

(71) Applicant: CANON KABUSHIKI KAISHA, Tokyo (JP)

(72) Inventors: Takeshi Noda, Ebina (JP); Yoshihito Machida, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 205 days.

(21) Appl. No.: 16/778,037

(22) Filed: Jan. 31, 2020

(65) Prior Publication Data

US 2020/0163630 A1 May 28, 2020

Related U.S. Application Data

(63) Continuation of application No. PCT/JP2018/027035, filed on Jul. 19, 2018.

(30) Foreign Application Priority Data

Sep. 1, 2017 (JP) .............................. JP2017-168833

(51) Int. Cl.
*A61B 6/03* (2006.01)
*G01N 23/04* (2018.01)
(Continued)

(52) U.S. Cl.
CPC ............ *A61B 6/032* (2013.01); *A61B 6/4241* (2013.01); *A61B 6/461* (2013.01); *A61B 6/469* (2013.01);
(Continued)

(58) Field of Classification Search
CPC ..... A61B 6/032; A61B 6/4233; A61B 6/4241; A61B 6/461; A61B 6/469; A61B 6/481; A61B 6/482; A61B 6/503; A61B 6/504; A61B 6/5205; A61B 6/5217; G01N 23/046; G01N 23/083; G01N 2223/401;
(Continued)

(56) References Cited

U.S. PATENT DOCUMENTS 5,291,403 A 3/1994 Ito
8,565,489 B2 10/2013 Machida
(Continued)

FOREIGN PATENT DOCUMENTS

EP 1 341 125 A2 9/2003
EP 1 347 413 A1 9/2003
(Continued)

*Primary Examiner* — Mark R Gaworecki
(74) *Attorney, Agent, or Firm* — Venable LLP

(57) ABSTRACT

An information processing apparatus comprises: an obtainment unit configured to obtain a radiation image of a subject; a generation unit configured to generate, based on a plurality of radiation images obtained by radiation of mutually different spectra, a material characteristic image in which a region for each material can be extracted from the interior of the subject; and an image processing unit configured to perform processing of enhancing or attenuating, based on a position of a specific region in the material characteristic image, the specific region in the radiation image.

29 Claims, 10 Drawing Sheets

(51) Int. Cl.
  *G01N 23/083* (2018.01)
  *G06T 5/00* (2006.01)
  *G06T 5/50* (2006.01)
  *G01N 23/046* (2018.01)
  *A61B 6/00* (2006.01)

(52) U.S. Cl.
  CPC .............. *A61B 6/481* (2013.01); *A61B 6/482* (2013.01); *A61B 6/503* (2013.01); *A61B 6/504* (2013.01); *A61B 6/5205* (2013.01); *A61B 6/5217* (2013.01); *G01N 23/046* (2013.01); *G01N 23/083* (2013.01); *G06T 5/002* (2013.01); *G06T 5/004* (2013.01); *G06T 5/008* (2013.01); *G06T 5/50* (2013.01); *A61B 6/4233* (2013.01); *G01N 2223/401* (2013.01); *G01N 2223/419* (2013.01); *G01N 2223/612* (2013.01); *G06T 2207/10081* (2013.01); *G06T 2207/10116* (2013.01); *G06T 2207/20016* (2013.01); *G06T 2207/30004* (2013.01)

(58) Field of Classification Search
  CPC ........ G01N 2223/419; G01N 2223/612; G06T 5/002; G06T 5/004; G06T 5/008; G06T 5/50; G06T 2207/10081; G06T 2207/10116; G06T 2207/20016; G06T 2207/30004
  See application file for complete search history.

(56) References Cited

U.S. PATENT DOCUMENTS

| | | | |
|---|---|---|---|
| 8,655,034 | B2 | 2/2014 | Noda |
| 8,675,946 | B2 | 3/2014 | Sakaguchi et al. |
| 8,744,210 | B2 | 6/2014 | Noda |
| 8,923,589 | B2 | 12/2014 | Noda |
| 9,014,450 | B2 | 4/2015 | Noda |
| 9,265,474 | B2 | 2/2016 | Machida |
| 9,820,713 | B2 | 11/2017 | Noda |
| 9,953,414 | B2 | 4/2018 | Noda |
| 2008/0232668 | A1 | 9/2008 | Kitamura |
| 2009/0304249 | A1 | 12/2009 | Wu |
| 2010/0260386 | A1 | 10/2010 | Machida |
| 2013/0121465 | A1 | 5/2013 | Cho |
| 2019/0320993 | A1 | 10/2019 | Noda et al. |

FOREIGN PATENT DOCUMENTS

| | | | |
|---|---|---|---|
| JP | H04-156689 | | 5/1992 |
| JP | H09-069157 | | 3/1997 |
| JP | 2006-026198 | | 2/2006 |
| JP | 2006026198 A | * | 2/2006 |
| JP | 2009-118985 | | 6/2009 |
| JP | 2010-131263 | | 6/2010 |
| JP | 2017-000675 | | 1/2017 |
| JP | 2017000675 A | * | 1/2017 |

* cited by examiner

| MATERIAL | EFFECTIVE ATOMIC NUMBER |
|---|---|
| FAT | 5.9~6.5 |
| MUSCLE | 7.4~7.6 |
| BONE | 12.3~13.8 |
| TITANIUM | 22 |
| STAINLESS STEEL | 26 |
| IODINE | 53 |
| BARIUM | 56 |

INFORMATION PROCESSING APPARATUS, RADIATION IMAGING APPARATUS, INFORMATION PROCESSING METHOD, AND STORAGE MEDIUM

CROSS-REFERENCE TO RELATED APPLICATIONS

This application is a Continuation of International Patent Application No. PCT/JP2018/027035, filed Jul. 19, 2018, which claims the benefit of Japanese Patent Application No. 2017-168833, filed Sep. 1, 2017, both of which are hereby incorporated by reference herein in their entirety.

BACKGROUND OF THE INVENTION

Field of the Invention

The present invention relates to an information processing apparatus, a radiation imaging apparatus, an information processing method, and a storage medium.

Background Art

As an imaging apparatus to be used for medical image diagnosis by radiation, a radiation imaging apparatus using a flat panel detector (to be referred to as an "FPD" hereinafter) has become popular. Since an FPD can perform digital image processing on a captured image, various kinds of applications have been developed and put into practical use.

As one such application, PTL 1 proposes an image processing technique capable of selectively performing frequency processing only on the shadow of a desired tissue using images captured by two types of radiation energies.

CITATION LIST

Patent Literature

PTL 1: Japanese Patent Laid-Open No. H04-156689

PTL 1 described, as a method of selectively performing frequency processing only on the shadow of a desired tissue, a method of adding the high-frequency component of an extracted image to an original image. However, when the extracted image and the original image represent different physical quantities, for example, the original image is a radiation image and the extracted image is an effective atomic number image, the method described in PTL 1 cannot be used.

The present invention has been made in consideration of the above-described problem and has as its object to provide a technique of enhancing or attenuating, based on the position of a specific region in a material characteristic image, the specific region in a corresponding radiation image.

SUMMARY OF THE INVENTION

According to one aspect of the present invention, there is provided an information processing apparatus comprising: an obtainment unit configured to obtain a radiation image of a subject; a generation unit configured to generate, based on a plurality of radiation images obtained by radiation of mutually different spectra, a material characteristic image in which a region for each material can be extracted from the interior of the subject; and an image processing unit configured to perform processing of enhancing or attenuating, based on a position of a specific region in the material characteristic image, the specific region in the radiation image.

According to another aspect of the present invention, there is provided an information processing apparatus comprising: an obtainment unit configured to obtain a radiation image of a subject; a generation unit configured to generate, based on pixel values of the radiation image and a variance of the pixel values, a material characteristic image in which a region for each material can be extracted from the interior of the subject; and an image processing unit configured to perform processing of enhancing or attenuating, based on a position of a specific region in the material characteristic image, the specific region in the radiation image.

Further features of the present invention will become apparent from the following description of exemplary embodiments with reference to the attached drawings.

DESCRIPTION OF THE EMBODIMENTS

Embodiments of the present invention will be described in detail below with reference to the accompanying drawings. Note that the constituent elements described in the embodiments are merely examples. The technical scope of the present invention is determined by the scope of the appended claims and is not limited by the individual embodiments to be described below.

First Embodiment

Figure 1:
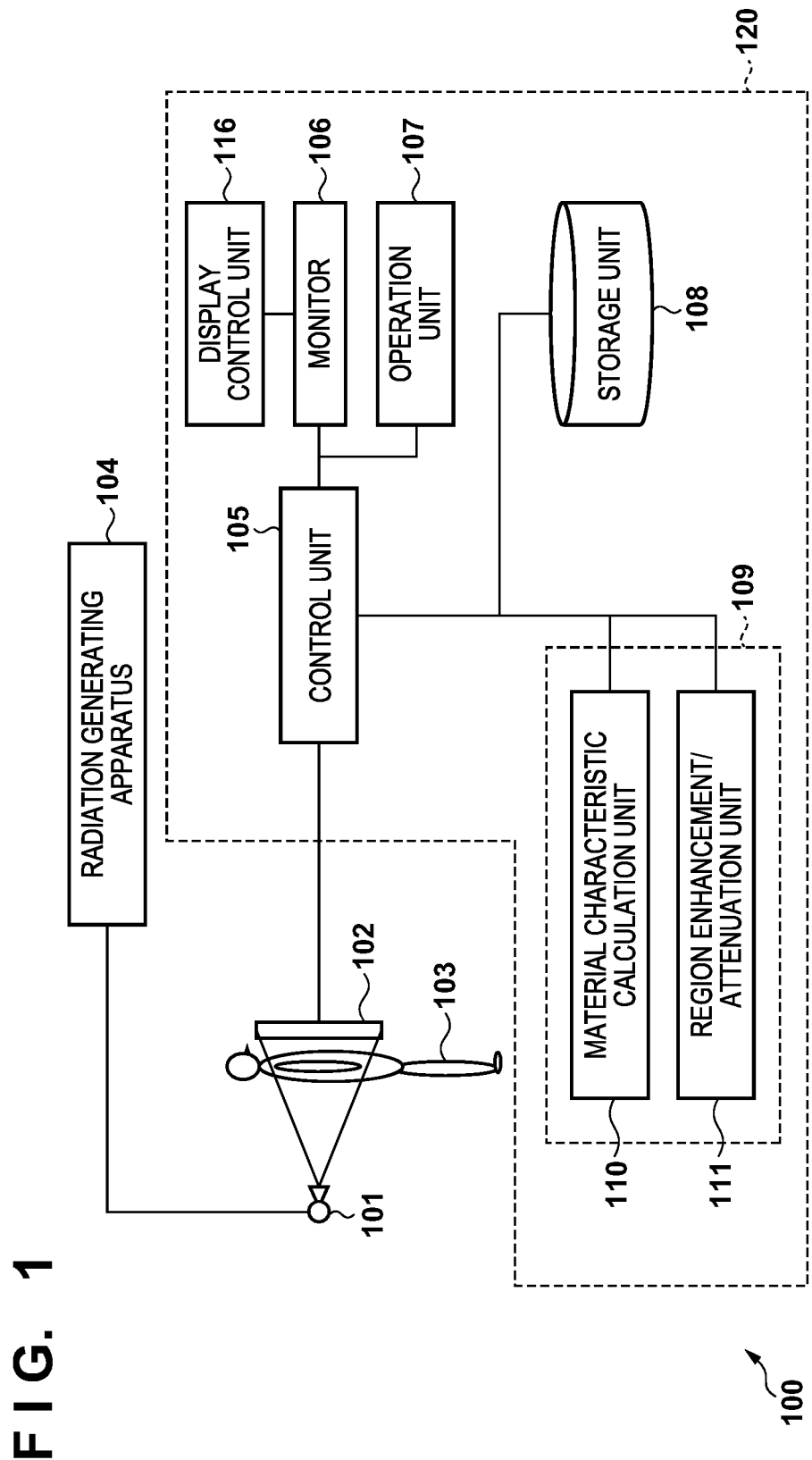
FIG. 1 is a block diagram showing an example of the arrangement of a radiation imaging system according to the first embodiment.

FIG. 1 is a block diagram showing an example of the arrangement of a radiation imaging system 100 according to the first embodiment of the present invention. The radiation imaging system 100 includes a radiation generating apparatus 104, a radiation source 101, an FPD 102, and an information processing apparatus 120. Note that the arrangement of the radiation imaging system 100 may also be called simply a radiation imaging apparatus. The information processing apparatus 120 processes information based a radiation image that has captured a subject.

The radiation generating apparatus 104 generates radiation by applying a high-voltage pulse to the radiation source 101 when an exposure switch is pressed. The radiation source 101 irradiates a subject 103 with radiation. Note that the type of radiation is not particularly limited, but an X-ray is often used in general.

When the subject 103 is irradiated with radiation from the radiation source 101, the FPD 102 obtains a radiation image by accumulating charges based on an image signal. The FPD 102 transfers the radiation image to the information processing apparatus 120. Note that the FPD 102 may transfer the radiation image to the information processing apparatus 120 for each imaging operation, or can store the captured image in an image storage unit in the FPD 102 without transferring the image for each image and transfer the stored images all together from the FPD 102 to the information processing apparatus 120 at a predetermined timing. The communication between the FPD 102 and the information processing apparatus 120 may be performed by wired communication or wireless communication.

The FPD 102 includes a radiation detection unit (not shown) in which a pixel array for generating a signal corresponding to the radiation is arranged. The radiation detection unit detects radiation that has been transmitted through the subject 103 as image signals. Pixels that output signals corresponding to incident light are arranged in an array (two-dimensional region) in the radiation detection unit. A photoelectric conversion element of each pixel converts light which has been converted by a fluorescent material into an image signal as an electric signal, and outputs it as the image signal. In this manner, the radiation detection unit is configured to detect radiation transmitted through the subject 103 and obtain image signals (radiation image). A driving unit (not shown) of the FPD 102 outputs, to a control unit 105, the image signals (radiation image) read out in accordance with the instruction from the control unit 105.

The control unit 105 includes an image processing unit 109 that processes a radiation image obtained from the FPD 102 and a storage unit 108 that stores the result of the image processing and various kinds of programs. The storage unit 108 is formed by, for example, a ROM (Read Only Memory), a RAM (Random Access Memory), or the like. The storage unit 108 can store an image output from the control unit 105, an image processed by the image processing unit 109, and calculation results obtained by the image processing unit 109. The storage unit 108 can store, for example, an effective atomic number, a surface density, and a database in which effective atomic numbers and materials have been associated.

The image processing unit 109 includes, as functional components, a material characteristic calculation unit 110 and a region enhancement/attenuation unit 111. According to these functional components, the function of each unit is implemented by one or a plurality of CPUs (Central Processing Units) using a program loaded from the storage unit 108. The configuration of each unit of the image processing unit 109 may be formed by an integrated circuit or the like as long as a similar function can be achieved. In addition, as the internal components of the information processing apparatus 120, it may be formed so as to include a graphic control unit such as a GPU (Graphics Processing Unit) or the like, a communication unit such as a network card or the like, an input/output control unit such as a keyboard, a display, or a touch panel, and the like can be included.

A monitor 106 (display unit) displays a radiation image (digital image) received by the control unit 105 from the FPD 102 and an image that has been processed by the image processing unit 109. A display control unit 116 can control the display operation of the monitor 106 (display unit). An operation unit 107 can input instructions to the image processing unit 109 and the FPD 102 and accepts the input of instructions to the FPD 102 via a user interface (not shown).

The image processing unit 109 includes, as functional components, the material characteristic calculation unit 110 and the region enhancement/attenuation unit 111, and the image processing unit 109 generates a region-enhanced image obtained by enhancing a specific region in the radiation image of the subject captured by the FPD 102, or a region-attenuated image obtained by attenuating the specific region. The material characteristic calculation unit 110 functions as a generation unit that generates a material characteristic image in which a region for each material can be extracted from the interior of the subject based on a plurality of radiation images obtained by radiation of mutually different spectra. As a material characteristic image, the material characteristic calculation unit 110 (generation unit) can generate, for example, a material characteristic image such as an effective atomic number image indicating the distribution of the effective atomic number of a material forming the subject or a material decomposition image in which a material forming the subject has been decomposed.

Figure 2:
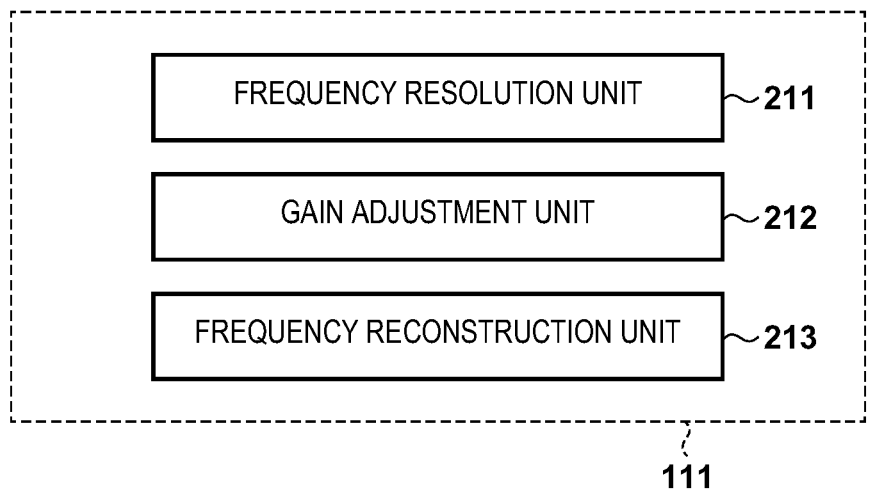
FIG. 2 is a block diagram showing an example of the functional arrangement of a region enhancement/attenuation unit.

The region enhancement/attenuation unit 111 performs image processing for enhancing or attenuating the radiation image based on the material characteristic image. That is, the region enhancement/attenuation unit 111 of the image processing unit 109 performs processing of enhancing or attenuating a specific region in the radiation image based on the position (position information) of the specific region in the material characteristic image. As shown in FIG. 2, the region enhancement/attenuation unit 111 includes, as functional components, a frequency resolution unit 211, a gain adjustment unit 212, and a frequency reconstruction unit 213. The specific processing of each of the frequency resolution unit 211, gain adjustment unit 212, and frequency reconstruction unit 213 will be described later in detail.

Figure 3:
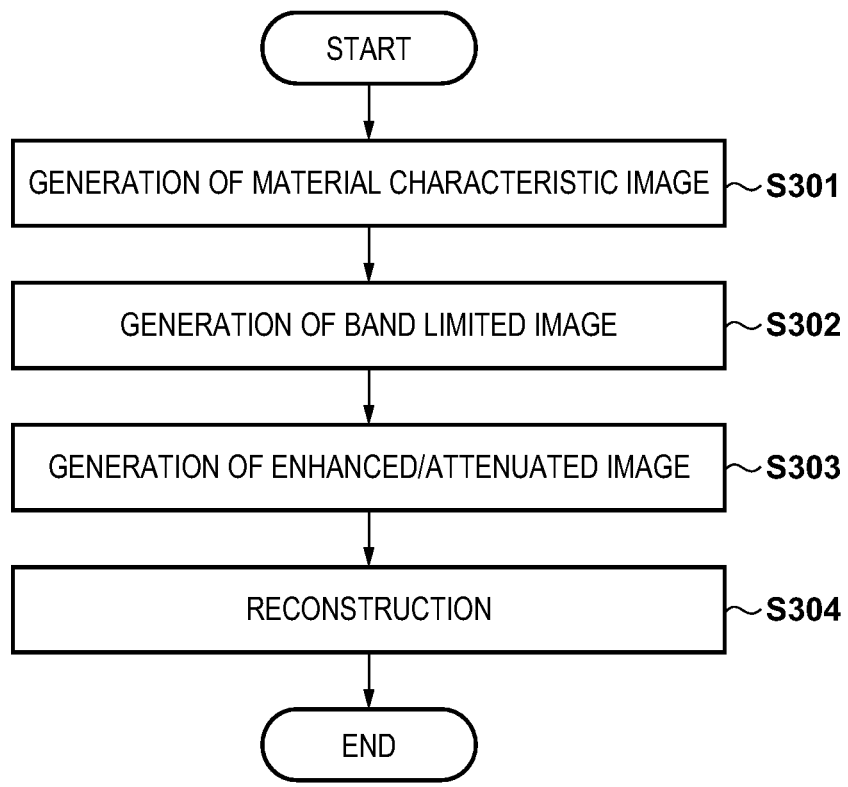
FIG. 3 is a flowchart for explaining the procedure of processing in an image processing unit according to the first embodiment.

Next, the processing performed in the image processing unit 109 according to the first embodiment will be described in detail with reference to the flowchart shown in FIG. 3. The control unit 105 stores each radiation image captured by the FPD 102 in the storage unit 108 and transfers the radiation image to the image processing unit 109.

(Step S301: Generation of Material Characteristic Image)

In step S301, the material characteristic calculation unit 110 generates a material decomposition image or an effective atomic number image serving as a material characteristic image. More specifically, the material characteristic calculation unit 110 generates a material decomposition image from a high-energy radiation image $X_H$ and a low-energy radiation image $X_L$ captured by the FPD 102 based on following equations (1) and (2).

$$-\ln X_L = \mu_{LA} d_A + \mu_{L1} d_I \qquad (1)$$

$$-\ln X_H = \mu_{HA} d_A + \mu_{H1} d_I \qquad (2)$$

Here, μ represents a radiation attenuation coefficient, and d represents the thickness of the material. Subscripts H and L indicate high energy and low energy, respectively. Each of subscripts A and I indicates a material to be decomposed, and herein, they indicate fat and a radiopaque dye, respectively. Note that fat and a radiopaque dye are used here as examples of the materials to be decomposed, but the material is not limited to these examples, and an arbitrary material can be decomposed. The material characteristic calculation unit 110 can obtain a material decomposition image in which fat $d_A$ and a radiopaque dye $d_I$ have been decomposed by performing arithmetic processing of solving the simultaneous equations of equations (1) and (2).

Figure 4:
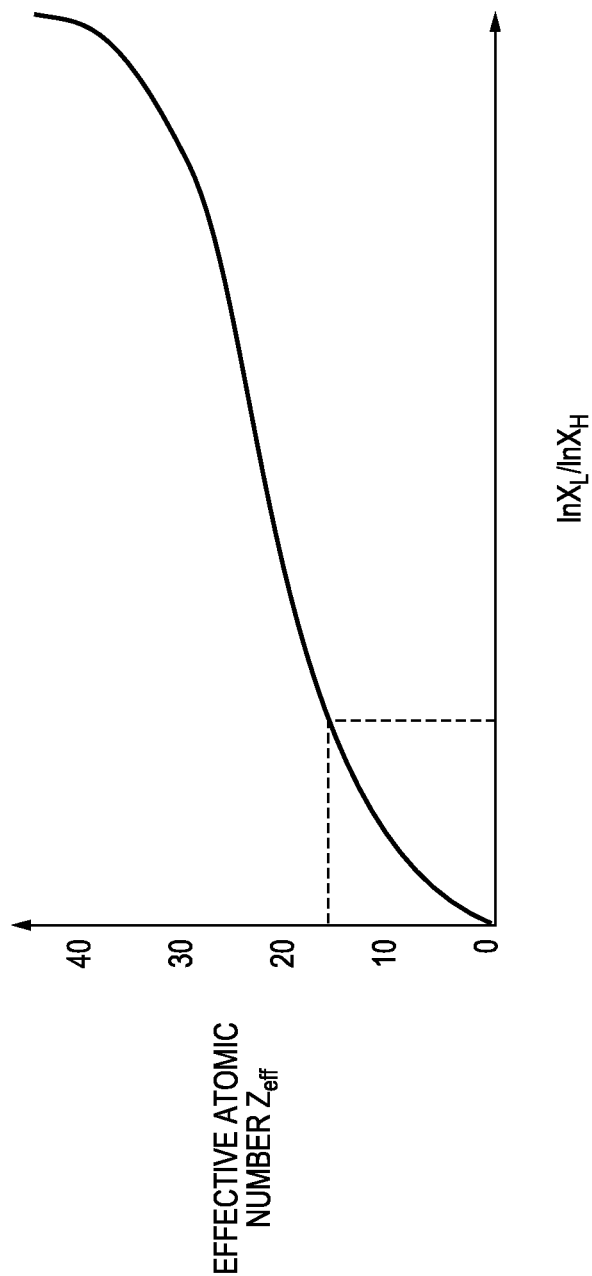
FIG. 4 is a graph for explaining generation of an effective atomic number image according to the first embodiment.
Figures 5, 6:
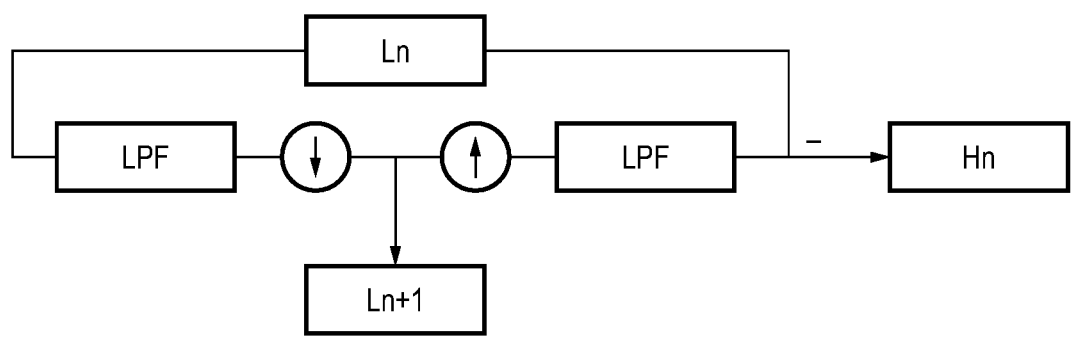
FIG. 5 is a table showing an example of an effective atomic number of each material.
FIG. 6 is a view for explaining the outline of frequency resolution processing.

In addition, the material characteristic calculation unit 110 can specify, from the logarithm of the ratio (logarithmic ratio) of the high-energy radiation image $X_H$ and the low-energy radiation image $X_L$ as shown in FIG. 4, a corresponding effective atomic number $Z_{eff}$ and generate an effective atomic number image Z. The relationship between the logarithmic ratio and an effective atomic number as shown in FIG. 4 is tabulated in advance, and the material characteristic calculation unit 110 can identify the effective atomic number $Z_{eff}$ corresponding to the calculated logarithmic ratio by referring to the table, and generate the effective atomic number image Z. FIG. 5 is a table showing an example of the effective atomic number of a material. For example, the effective atomic number of fat ranges from 5.9 to 6.5, the effective atomic number of muscle ranges from 7.4 to 7.6, and the effective atomic number of bone ranges from 12.3 to 13.8. In this manner, a specific region forming a human body (subject) such as fat, muscle, or bone can be specified by the effective atomic number.

The effective atomic number of iodine contained in a radiopaque dye or the like is 53, the effective atomic number of barium is 56, and the effective atomic number of stainless steel as a member used for a guide wire for a catheter or the like is 26. The effective atomic number of titanium as a member used for a stent is 22. By using the effective atomic number information, it is possible to decompose a material in a human body (subject) in accordance with the imaging technique.

In the following processing, the region enhancement/attenuation unit 111 performs image processing of enhancing or attenuating the radiation image based on the material characteristic image generated by the material characteristic calculation unit 110. That is, the region enhancement/attenuation unit 111 performs image processing of selectively enhancing/attenuating the radiation image based on the material decomposition image or the effective atomic number. In particular, the effective atomic number image is an image representing the distribution of the effective atomic number of the material forming the subject, and represents a physical quantity completely different from that represented in the original radiation image. For this reason, a method such as adding an image component cannot be used to selectively enhance/attenuate the radiation image, but according to the image processing of this embodiment, it is possible to selectively enhance/attenuate a specific region (a region of a decomposed material or a distribution region of an effective atomic number) in the radiation image.

(Step S302: Generation of Band limited Image)

In step S302, the frequency resolution unit 211 performs frequency resolution on the radiation image and the material characteristic image, and generates a plurality of band limited images (high-frequency images) limited to different frequency bands from each of the radiation image and the material characteristic image. In this step, the frequency resolution unit 211 resolves each of the radiation image and the material characteristic image into a plurality of band limited images limited to different frequency bands and a low-frequency image. By performing frequency resolution on both of the radiation image and the material characteristic image, the positional relationship of the regions in both images can be maintained.

FIG. 6 is a view for explaining the outline of frequency resolution processing. As shown in FIG. 6, the frequency resolution unit 211 performs anti-aliasing processing on an input image Ln (each of radiation image and material characteristic image) using a low-pass filter (LPF) and performs down-sampling (↓) of ½ times with respect to the processed image, thereby obtaining a low-frequency image Ln+1.

Further, the frequency resolution unit 211 performs two-fold up-sampling (↑) with respect to the low-frequency image Ln+1, performs anti-aliasing processing using the low-pass filter (LPF), and performs difference processing (−) between the processed image and the input image Ln, thereby obtaining a band limited image Hn. By sequentially performing the above-described processing, the frequency resolution unit 211 can generate the n-level low-frequency image Ln and the band limited image Hn obtained by performing frequency resolution on the input image Ln (each of the radiation image and material characteristic image). Thus, a plurality of band limited images are generated.

Figure 7:
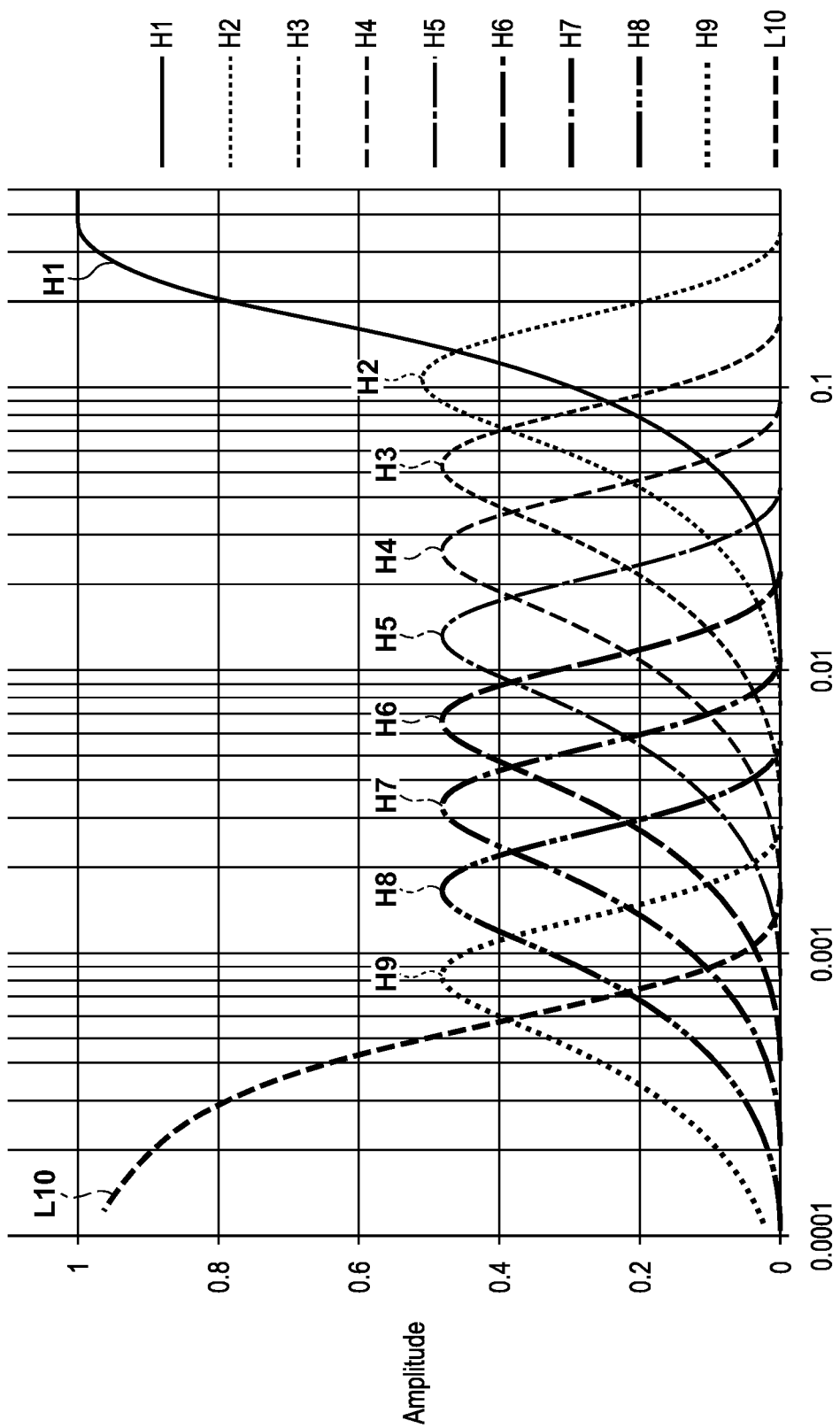
FIG. 7 is a graph showing an example of the frequency characteristic of each band limited image.

FIG. 7 is a graph showing an example of the frequency characteristic of each of band limited images generated by the processing in step S302, in which the abscissa represents the normalized frequency, and the ordinate represents the amplitude. In the following description, an n-level low-frequency radiation image obtained by performing frequency resolution on a radiation image is denoted by LXn, a band limited radiation image obtained thereby is denoted by HXn, an n-level low-frequency material characteristic image obtained by performing frequency resolution on a material characteristic image is denoted by LMn, and a band limited material characteristic image obtained thereby is denoted by HMn.

(Step S303: Generation of Enhanced/Attenuated Image)

In this step, the gain adjustment unit 212 of the image processing unit 109 sets, based on the position of the specific region in the material characteristic image resolved into the low-frequency image, an adjustment coefficient (gain) for enhancing or attenuating the specific region in each of the band limited images and low-frequency image of the radiation image.

In addition, the gain adjustment unit 212 sets, based on the position of the specific region in the material characteristic image resolved into the low-frequency image, an adjustment coefficient (gain) for enhancing or attenuating a region other than the specific region. Here, the gain adjustment unit 212 can set different adjustment coefficients (gains) for the specific region in the band limited image and the specific region in the low-frequency image of the radiation image, and the gain adjustment unit 212 can set different adjustment coefficients (gains) for the specific region and the region other than the specific region.

Figure 8:
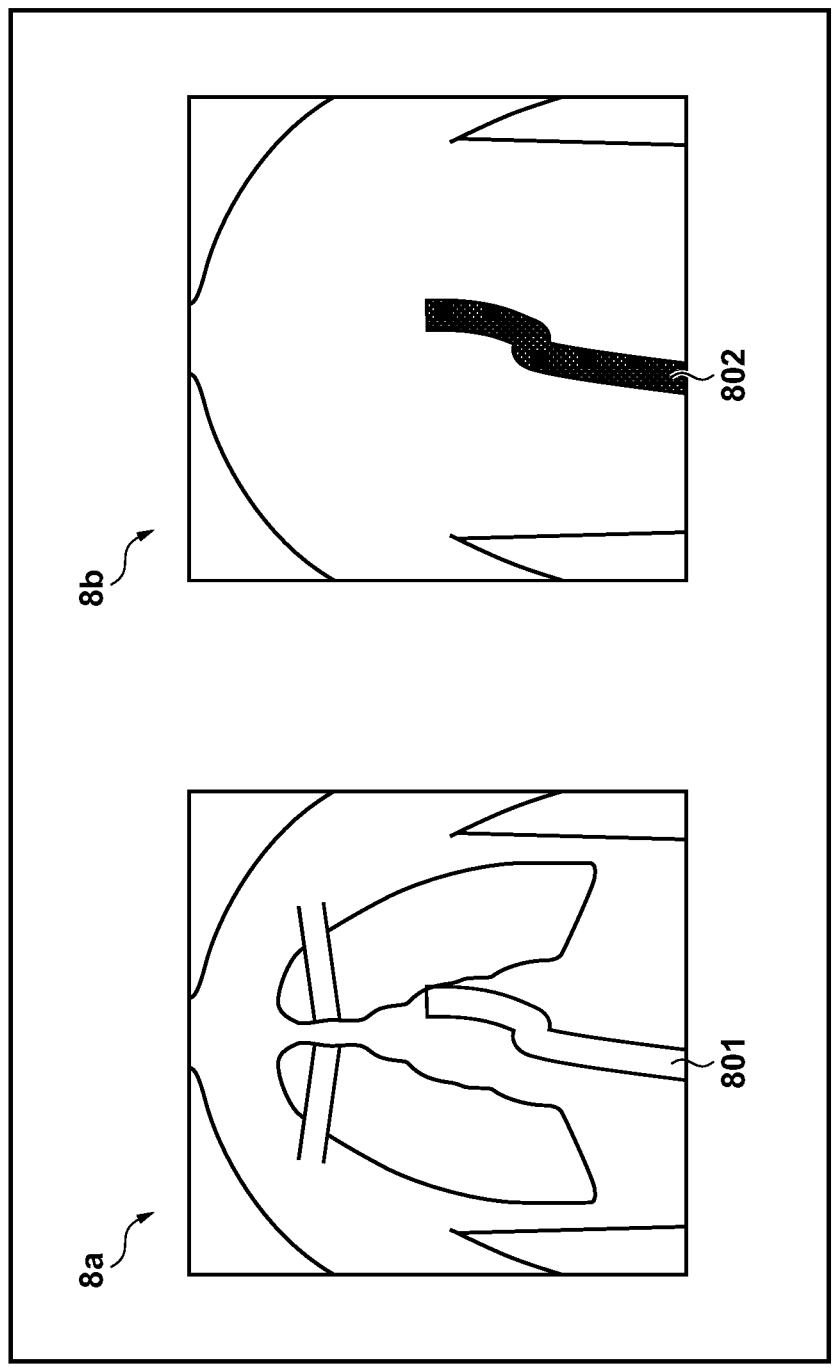
FIG. 8 shows examples of a radiation image 8a and a material characteristic image 8b.

More specifically, the gain adjustment unit 212 adjusts the gain for the specific region in each of the band limited radiation image HXn and the low-frequency radiation image LXn based on the position of the specific region in the low-frequency material characteristic image LMn. FIG. 8 shows examples of a radiation image 8a and a material characteristic image 8b, each of which schematically depicts a human body. In the radiation image 8a in FIG. 8, a region 801 represents a blood vessel contrast-enhanced by a radiopaque dye. In a material characteristic image such as a material decomposition image or an effective atomic number image, a high pixel value or effective atomic number is expressed in a radiopaque dye (including iodine) portion. Therefore, in the material characteristic image 8b in FIG. 8, a radiopaque dye portion can be extracted as in a region 802 by threshold processing or the like.

In the processing method described in PTL 1, frequency resolution processing for obtaining a high-frequency component is performed on the portion of the region 802 in the material characteristic image 8b in FIG. 8, and the high-frequency component is added to the radiation image 8a in FIG. 8. However, such a method of adding an image component can be applied to a material decomposition image serving as a material characteristic image, but cannot be used for an image such as an effective atomic number image which represents the physical quantity different from that represented in the original radiation image.

Also, even in the case of an image such as a material decomposition image which has the same physical quantity as the original radiation image, in general, when a high-frequency component of only a predetermined region is enhanced and added in each of different images, artifacts are likely to occur due to inconsistencies with other regions.

Figure 9:
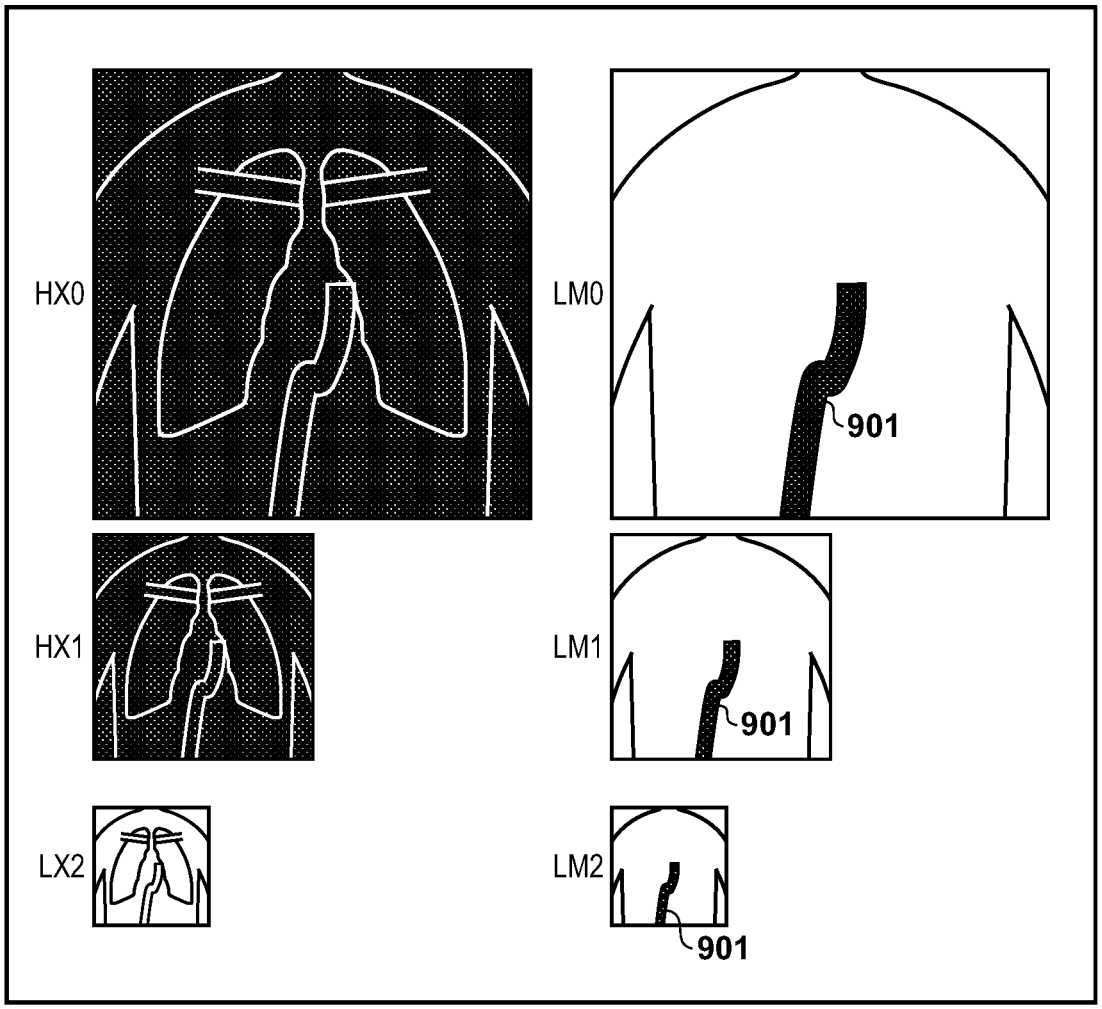
FIG. 9 is a view for explaining gain adjustment based on a low-frequency material characteristic image.

Therefore, in this embodiment, as shown in FIG. 9, the gain adjustment unit 212 performs gain adjustment based on the low-frequency material characteristic image LMn corresponding to the frequency resolution level with respect to the images (band limited radiation image HXn and low-frequency radiation image LXn) obtained by resolving the radiation image into respective frequency bands.

In FIG. 9, a low-frequency material characteristic image LM0 corresponds to a band limited radiation image HX0. Further, a low-frequency material characteristic image LM1 corresponds to a band limited radiation image HX1, and a low-frequency material characteristic image LM2 corresponds to a band limited radiation image HX2. Note that in the example shown in FIG. 9, the order of resolution level is set to 2 (n=2) for descriptive convenience. However, the order of resolution level is not limited to this example and arbitrarily set.

The image processing unit 109 can refer to the position of a region in the material characteristic image and perform image processing of enhancing or attenuating a specific region in the radiation image corresponding to the position of the region in the material characteristic image. Further, the image processing unit 109 can refer to the position of a region in the material characteristic image and perform image processing of enhancing or attenuating a region other than a specific region obtained by excluding the specific region in the radiation image corresponding to the position of the region in the material characteristic image.

In each of the low-frequency material characteristic images LMn (n=0, 1, 2) shown in FIG. 9, the gain adjustment unit 212 indicates the position of a specific region in the low-frequency material characteristic image LMn by a radiopaque dye region 901. In the low-frequency image and band limited image (low-frequency radiation image Ln and band limited radiation image Hn (n=0, 1, 2)) of the radiation image, a specific region corresponding to the radiopaque dye region 901 or a region other than the specific region is multiplied by an arbitrary gain, so that image processing of enhancing or attenuating either one of the specific region and the region other than the specific region is performed.

That is, the image processing unit 209 refers to the position of the specific region in the material characteristic image and performs image processing of enhancing or attenuating either one of the specific region and the region other than the specific region in the radiation image. More specifically, the gain adjustment unit 212 multiplies each of the specific region in the radiation image corresponding to the radiopaque dye region 901 in the material characteristic image and a region other than the specific region by an arbitrary gain, thereby performing image processing of enhancing or attenuating each region. For example, the gain adjustment unit 212 refers to the position of the specific region (radiopaque dye region 901) in the material characteristic image and performs image processing of enhancing the specific region in the radiation image or attenuating the region other than the specific region in the radiation image. Here, the specific region and the region other than the specific region may be multiplied by different gain values, and the gain adjustment unit 212 can arbitrarily change the gain values in accordance with the images HXn and LXn. Hereinafter, the gain-adjusted band limited image and gain-adjusted low-frequency image of the radiation image are denoted by HXGn and LXGn, respectively.

When the gain value used for gain adjustment is set to be larger than 1, the corresponding band limited image is enhanced, and when the gain value is set to be smaller than 1, the band limited image is attenuated (suppressed). For example, by setting different gain values for different frequency resolution levels, the gain adjustment unit 212 can generate images having various frequency enhancements or suppressions.

Based on the set gain, the image characteristic of the specific region or the region other than the specific region in the radiation image can be enhanced or attenuated.

(Step S304: Reconstruction Processing)

Figure 10:
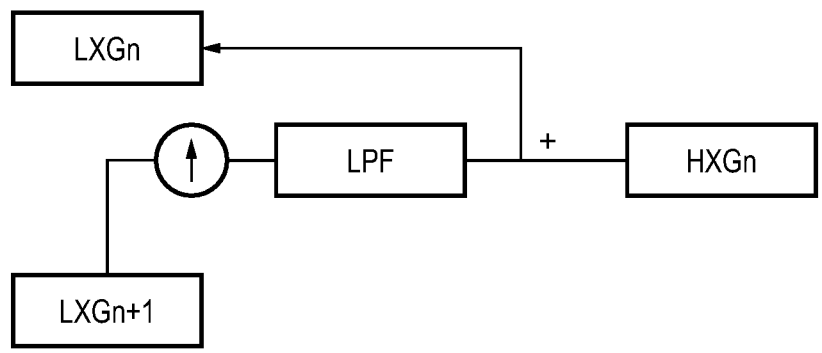
FIG. 10 is a view for explaining the outline of radiation image reconstruction processing.

In step S304, the frequency reconstruction unit 213 reconstructs the radiation images (band limited image HXGn and low-frequency image LXGn) which have undergone the gain adjustment in step S303. More specifically, as shown in FIG. 10, the frequency reconstruction unit 213 performs up-sampling (↑) with respect to the low-frequency image LXGn+1 among the images obtained by performing frequency resolution on the radiation image and performs anti-aliasing processing on the up-sampled image using a low-pass filter (LPF), thereby generating an enlarged image. In addition, the frequency reconstruction unit 213 generates the low-frequency image LXGn of the radiation image by adding the band limited image HXGn of the radiation image to the generated enlarged image. The low-frequency image LXGn having a frequency resolution level of n is generated from the low-frequency image having a frequency resolution level of n+1.

The frequency reconstruction unit 213 sequentially performs the above-described processing to generate a low-frequency image LXG0 of the radiation image. When the gain adjustment is not performed, the low-frequency image LXG0 matches the original radiation image (the radiation image 8a in FIG. 8). When gain adjustment is performed, an image in which the region 801 (specific region) in the radiation image 8a in FIG. 8 has been enhanced or attenuated or an image in which a region other than the region 801 (specific region) has been enhanced or attenuated is generated. With this processing, the processing performed in the image processing unit 109 ends.

Figure 11:
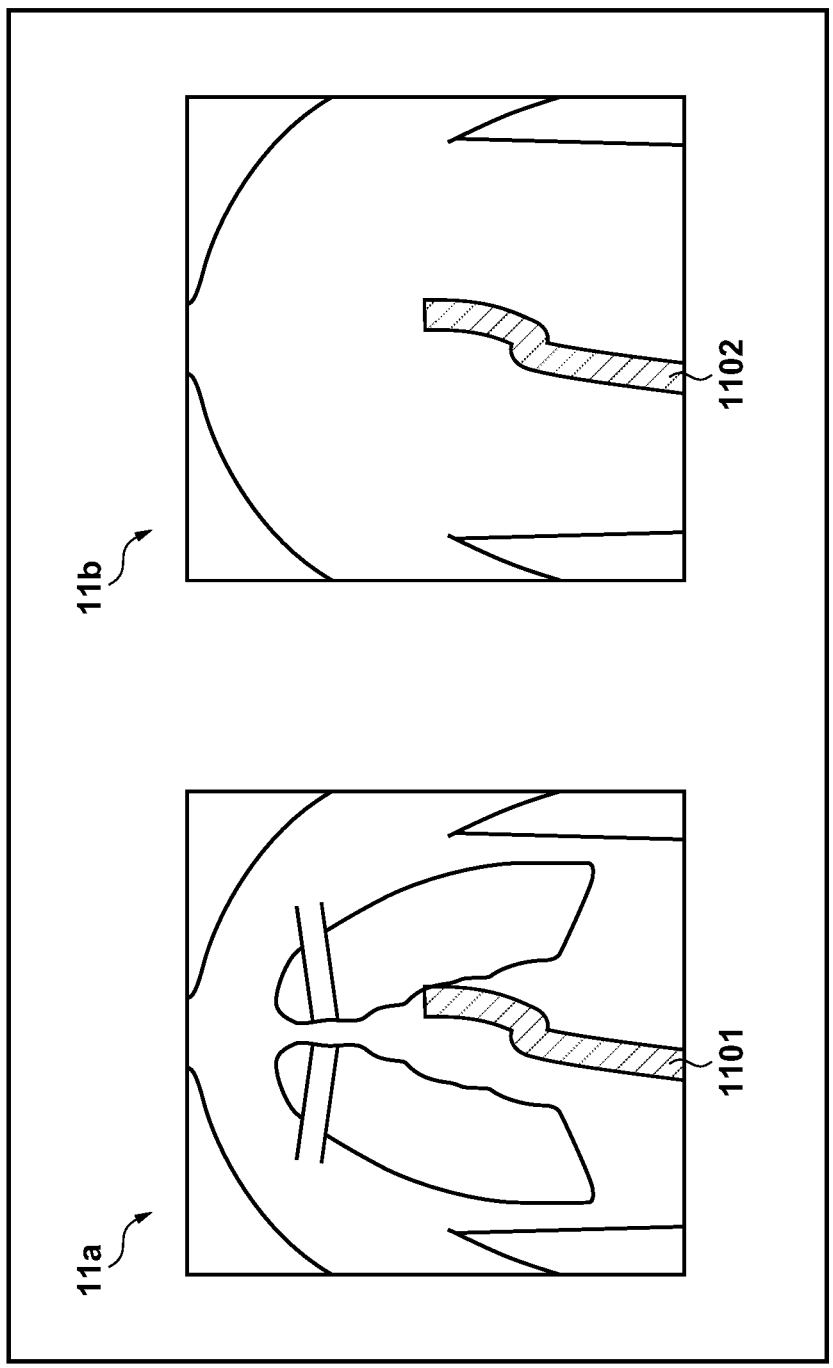
FIG. 11 is a view showing an example of the processing result of the image processing unit according to the first embodiment.

FIG. 11 is a view showing an example of the processing result of the image processing unit 109 according to the first embodiment. FIG. 11 shows a radiation image 11a, and a radiopaque dye region 1101 is a region corresponding to the region 801 in the radiation image 8a in FIG. 8. According to the processing performed in the image processing unit 109, it is possible to obtain an image, such as the radiation image 11a in FIG. 11, in which the radiopaque dye region 1101 (the region corresponding to the region 801 (specific region) in the radiation image 8a in FIG. 8) of the radiation image has been enhanced.

In addition, the image processing unit 109 can generate a pseudo DSA (Digital Subtraction Angiography) image in which a radiopaque dye region 1102 has been extracted as illustrated in an image 11b in FIG. 11 by attenuating a region other than the radiopaque dye region 1101. Note that in the image 11b in FIG. 11, the image processing unit 109 can generate a more suitable pseudo DSA image by enhancing the radiopaque dye region 1102 while attenuating the region outside the radiopaque dye region. For example, the gain adjustment unit 212 of the image processing unit 109 performs gain adjustment by multiplying the region 801 (specific region) in the radiation image 8a in FIG. 8 by a gain that enhances the region 801 (specific region) and multiplying the region other than the region 801 (specific region) by a gain that attenuates a region other than the specific region, and the frequency reconstruction unit 213 reconstructs gain-adjusted radiation images (band limited image HXGn and low-frequency image LXGn). Thus, it is possible to generate a pseudo DSA image in which the radiopaque dye region 1102 has been enhanced while the region outside the radiopaque dye region has been attenuated.

According to this embodiment, even when the material characteristic image is an image such as an effective atomic number image whose characteristic is different from that of the radiation image, it is possible to appropriately enhance/attenuate the radiation image using the effective atomic number image. Further, it is possible to implement enhancement/attenuation processing that hardly causes artifacts by continuously performing gain adjustment with respect to the band limited image instead of enhancing only the high-frequency component in a specific region. An image obtained by selectively enhancing the radiopaque dye region leads to the implementation of a procedure with a lower amount of radiopaque dye. In addition, a pseudo DSA image obtained by selectively attenuating a region other than the radiopaque dye leads to the implementation of a DSA image (maskless DSA image) that does not use a mask image. This makes it possible to implement a medical technique that is minimally invasive and highly convenient.

Second Embodiment

In this embodiment, the arrangement of an information processing apparatus that generates a material characteristic image based on the variance value and average value of pixel values of a radiation image will be described. In the following description, a description of parts similar to the first embodiment will be omitted, and only component parts specific to the second embodiment will be described. The arrangement of this embodiment makes it possible to generate a material characteristic image even when radiation images having different spectra (for example, the high-energy radiation image $X_H$ and the low-energy radiation image $X_L$ described in the first embodiment) cannot be obtained, and enhance or attenuate a predetermined region in the radiation image using the generated material characteristic image.

Figure 12:
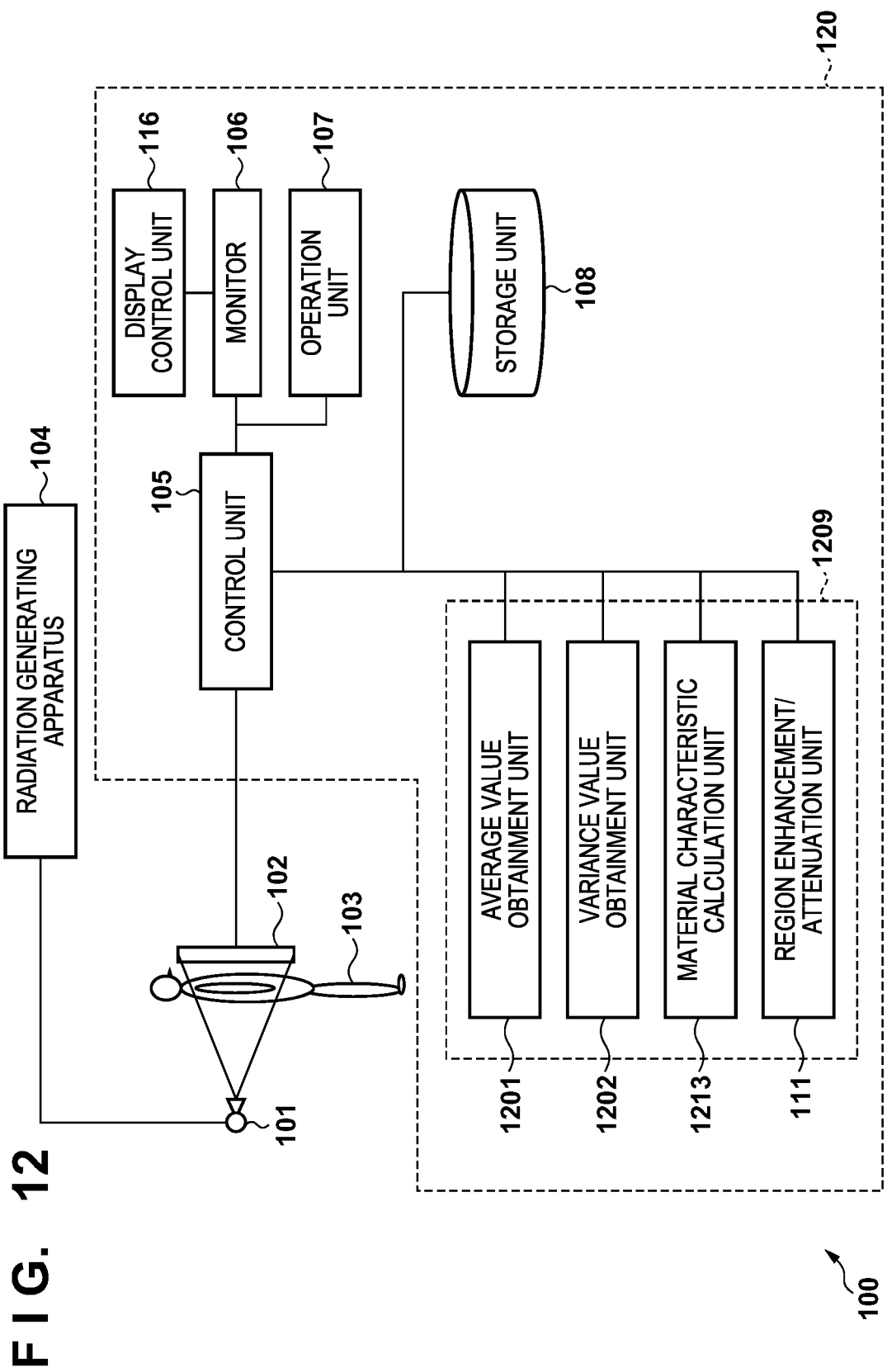
FIG. 12 is a block diagram showing an example of the arrangement of a radiation imaging system according to the second embodiment.
Figure 14:
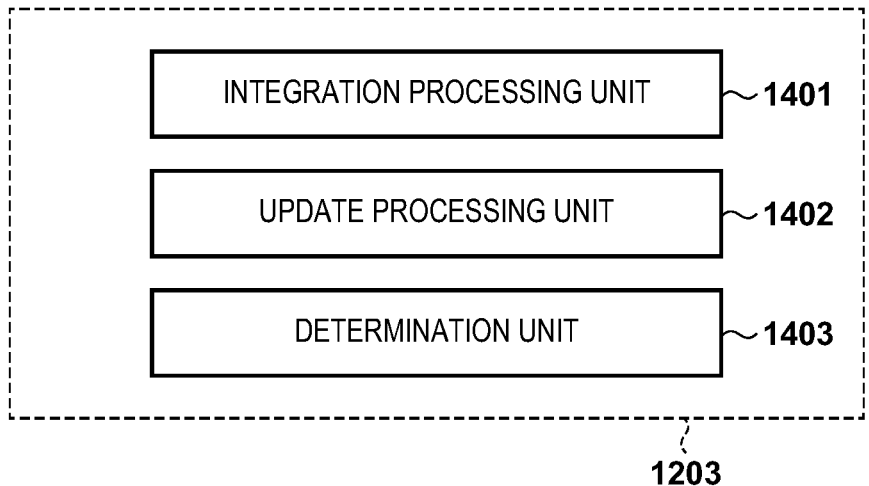
FIG. 14 is a block diagram showing an example of the functional arrangement of a material characteristic calculation unit.

FIG. 12 is a block diagram showing an example of the arrangement of a radiation imaging system 100 according to the second embodiment of the present invention. In this embodiment, an image processing unit 1209 includes an average value obtainment unit 1201 that obtains an average value of pixel values of a radiation image obtained by capturing a subject, a variance value obtainment unit 1202 that obtains a variance value of pixel values of a radiation image, a material characteristic calculation unit 1203, and a region enhancement/attenuation unit 111. Here, the material characteristic calculation unit 1203 generates, based on the pixel values of the radiation image and the variance of the pixel values, a material characteristic image in which a region for each material can be extracted from the interior of the subject. As shown in FIG. 14, the material characteristic calculation unit 1203 includes, as functional components, an integration processing unit 1401, an update processing unit 1402, and a determination unit 1403. In this embodiment, the arrangement of the image processing unit 1209 is different from that of the image processing unit 109 according to the first embodiment in that the average value obtainment unit 1201, variance value obtainment unit 1202, and material characteristic calculation unit 1203 are provided. The region enhancement/attenuation unit 111 performs processing of enhancing or attenuating a specific region in a radiation image based on the position of the specific region in a material characteristic image.

Figure 13:
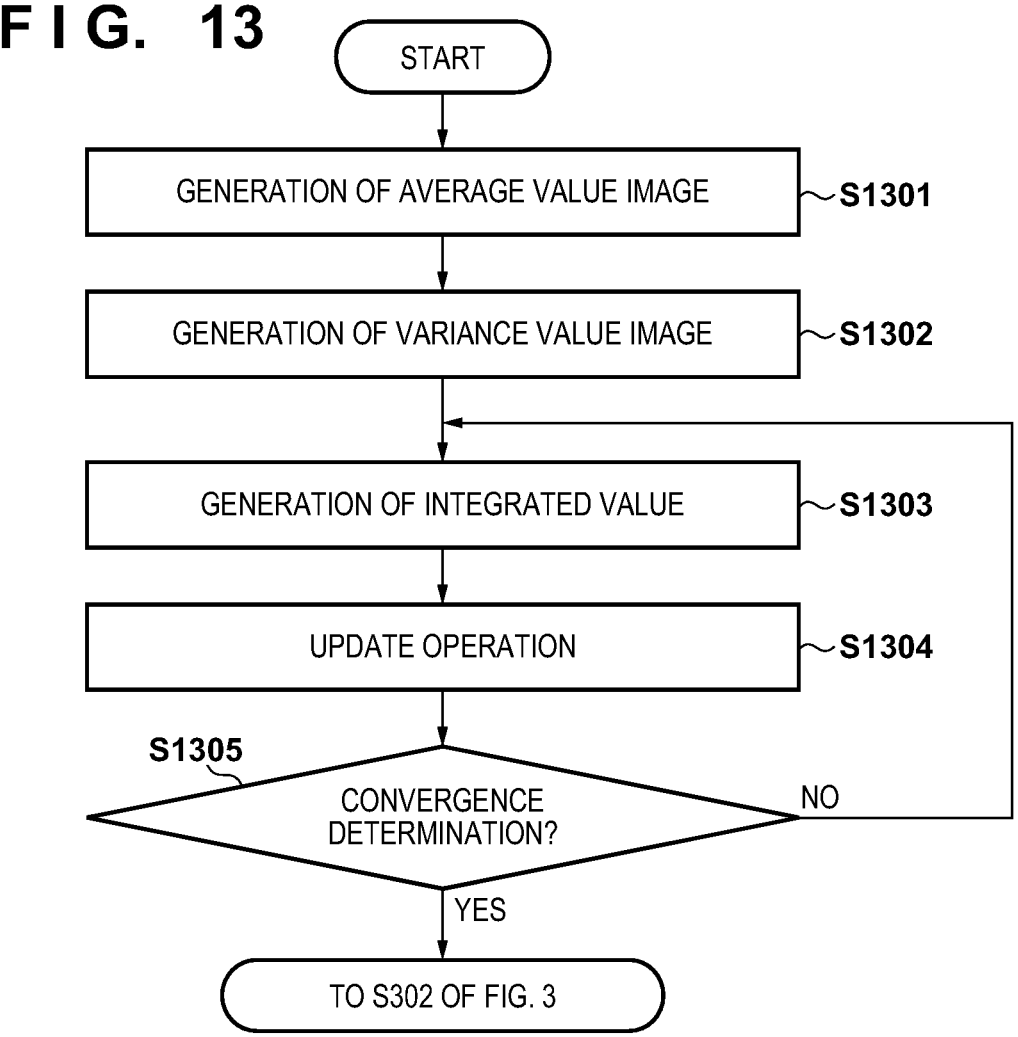
FIG. 13 is a flowchart for explaining the procedure of processing in an image processing unit according to the second embodiment.

Next, the processing performed in the image processing unit 1209 according to the second embodiment will be described in detail with reference to the flowchart shown in FIG. 13. A control unit 105 stores each radiation image captured by an FPD 102 in a storage unit 108 and transfers the radiation image to the image processing unit 1209.

(Step S1301: Generation of Average Information (Average Value Image))

In step S1301, the average value obtainment unit 1201 obtains an average value image which indicates an average value (average information) of pixel values obtained by dividing the pixel values of a radiation image with a subject by the pixel values of a radiation image without the subject. More specifically, the average value obtainment unit 1201 obtains (generates) an average value image A(x, y) by using a radiation image M(x, y, t) with the subject and a radiation image $M_0$(x, y, t) without the subject (equation (3)) that have been captured by the FPD 102. Here, x and y represent coordinates of a pixel of an image and t is an integer representing a frame number of an image captured in time series. Each bracket "< >t" represents a time average. The gain characteristic variation of the FPD 102 can be corrected by dividing the time average (average information) of the radiation image M with the subject by the time average (average information) of the radiation image $M_0$ without the subject. The radiation image $M_0$(x, y, t) without the subject is captured in advance and stored in the storage unit 108. The average value obtainment unit 1201 reads out the radiation image $M_0$(x, y, t) without the subject from the storage unit 108 when an average value image is to be obtained, and performs arithmetic processing of equation (3).

$$A(x, y) = \frac{<M(x, y, t)>_t}{<M_0(x, y, t)>_t} \quad (3)$$

(Step S1302: Generation of Variance Information (Variance Value Image))

In step S1302, the variance value obtainment unit 1202 obtains a variance value image which indicates the variance value (variance information) of the pixel values obtained by dividing the pixel value of the radiation image with the subject by the pixel value of the radiation image without the subject. More specifically, the variance value obtainment unit 1202 obtains (generates) a variance value image V(x, y) by using a plurality of the radiation images M(x, y, t) with the subject and the radiation image $M_0$(x, y, t) without the subject that have been captured by the FPD 102 (equation (4)). Here, x and y represent coordinates of a pixel of an image and t is an integer representing a frame number of an image captured in time series. Each bracket "< >t" represents a time average. The radiation image $M_0$(x, y, t) without the subject is captured in advance and stored in the storage unit 108. The variance value obtainment unit 1202 reads out the radiation image $M_0$(x, y, t) without the subject from the storage unit 108 when a variance value image is to be obtained, and performs arithmetic processing of equation (4).

$$V(x, y) = \frac{<M^2(x, y, t)>_t - <M(x, y, t)>_t^2}{<M_0^2(x, y, t)>_t - <M_0(x, y, t)>_t^2} \quad (4)$$

(Step S1303: Calculation of Parameters for Arithmetic Processing)

In step S1303, the integration processing unit 1401 of the material characteristic calculation unit 1203 calculates the following six parameters to be used to obtain the effective atomic number and the surface density of the material forming the subject.

Here, a parameter Ac of equation (5) is a theoretically calculated pixel value of the radiation image and corresponds to an average value (average information). A parameter Vc of equation (6) is a theoretically calculated pixel value of the radiation image and corresponds to a variance value (variance information). That is, the parameter Ac (average information) is the first moment of the energy, and the parameter Vc (variance information) is the second moment of the energy.

The parameters of equations (7) to (10) are the derivatives of the parameters Ac and Vc obtained by equations (5) and (6). The parameters obtained in step S1303 are used in the arithmetic processing (update operation) which is performed in the next step. These parameters are used in an iterative calculation performed in the update operation of step S1304.

$$Ac = \frac{\int_0^\infty N(E)\exp\{-\mu(Z_{eff}, E)\sigma_{eff}\}EdE}{\int_0^\infty N(E)EdE} \quad (5)$$

$$Vc = \frac{\int_0^\infty N(E)\exp\{-\mu(Z_{eff}, E)\sigma_{eff}\}E^2 dE}{\int_0^\infty N(E)E^2 dE} \quad (6)$$

$$\frac{\partial Ac}{\partial \sigma_{eff}} = \frac{\int_0^\infty -\mu(Z_{eff}, E)N(E)\exp\{-\mu(Z_{eff}, E)\sigma_{eff}\}EdE}{\int_0^\infty N(E)EdE} \quad (7)$$

$$\frac{\partial Vc}{\partial \sigma_{eff}} = \frac{\int_0^\infty -\mu(Z_{eff}, E)N(E)\exp\{-\mu(Z_{eff}, E)\sigma_{eff}\}E^2 dE}{\int_0^\infty N(E)E^2 dE} \quad (8)$$

$$\frac{\partial Ac}{\partial Z_{eff}} = \frac{\int_0^\infty -\frac{\partial \mu(Z_{eff}, E)}{\partial Z_{eff}}\sigma_{eff} N(E)\exp\{-\mu(Z_{eff}, E)\sigma_{eff}\}EdE}{\int_0^\infty N(E)EdE} \quad (9)$$

$$\frac{\partial Vc}{\partial Z_{eff}} = \frac{\int_0^\infty -\frac{\partial \mu(Z_{eff}, E)}{\partial Z_{eff}}\sigma_{eff} N(E)\exp\{-\mu(Z_{eff}, E)\sigma_{eff}\}E^2 dE}{\int_0^\infty N(E)E^2 dE} \quad (10)$$

Here, $\sigma_{eff}$ represents the surface density [g/cm$^2$] of the material, $\mu$ represents the attenuation coefficient [cm$^2$/g], $Z_{eff}$ represents the effective atomic number of the material, E represents the energy of the radiation, and N(E) represents the energy spectrum of the radiation.

In the obtainment of the rate of change of a pixel average value or the rate of change of a pixel variance value, the integration processing unit 1401 of the material characteristic calculation unit 1203 generates interpolation information for interpolating the attenuation coefficient by using the energy of the radiation, the atomic number of an already known element, and the attenuation coefficient corresponding to the atomic number. Also, in the obtainment of the rate of change of a pixel average value or the rate of change of a pixel variance value, the integration processing unit 1401 of the material characteristic calculation unit 1203 obtains the rate of change per unit atomic number of the attenuation coefficient which has been interpolated based on the interpolation information.

The interpolation information and the rate of change for each unit of atomic number of the interpolated attenuation coefficient can be represented as follows in the manner of equations (11) and (12) by using the energy (E) of the radiation, the atomic number (Z) of an already known element, and the attenuation coefficient corresponding to the atomic number (Z).

The integration processing unit 1401 can store the atomic number of the already known element and the corresponding attenuation coefficient in, for example, the storage unit 108, and use the atomic number of the already known element and the corresponding attenuation coefficient in the interpolation of the attenuation coefficient$\mu$ by referring to the storage unit 108. In addition, the integration processing unit 1401 generates change rate information (derivative) indicating the rate of change of the attenuation coefficient $\mu$ with respect to the change of the unit effective atomic number (equation (12)). Here, in equations (11) and (12), the term ([x]) indicates a floor function which outputs the maximum integer equal to x or less with respect to a real number x.

$$\mu(Z, E) = \mu(([Z] + 1, E) - \mu([Z], E))(Z - [Z]) + \mu([Z], E) \quad (11)$$

$$\frac{\partial \mu(Z, E)}{\partial Z} = \mu([Z] + 1, E) - \mu([Z], E) \quad (12)$$

(Step S1304: Update Operation of Effective Atomic Number and Surface Density)

In step S1304, the update processing unit 1402 of the material characteristic calculation unit 1203 obtains the effective atomic number and the surface density based on equations (13).

More specifically, the update processing unit 1402 of the material characteristic calculation unit 1203 updates the effective atomic number ($Z_{eff}$) of the material and the surface density ($\sigma_{eff}$) of the material by performing an iterative operation based on the calculation of equations (13) below. Here, the notation of "( )" represents a matrix, and "−1" represents an inverse matrix. In addition, the exponent n represents the number of times the iterative operation is performed.

In simultaneous equations (13), the derivatives of the parameters Ac and Vc are parameters obtained by the arithmetic processing of equations (7) to (10). Also, A represents information of the average value image (average information of pixel values of the radiation image) obtained by the arithmetic processing of equation (3), and Ac represents the average information of the pixel values of the radiation image based on the theoretical calculation of equation (5). In addition, in equations (13), V represents information of the variance value image (variance information of pixel values of the radiation image) obtained by the arithmetic processing of equation (4), and Vc represents the variance information of the pixel values of the radiation image based on the theoretical calculation of equation (6).

The update processing unit 1402 obtains the effective atomic number ($Z_{eff}$) and the surface density ($\sigma_{eff}$) of the material forming the subject by iteratively executing the arithmetic processing of equations (13). At this time, an arbitrary value such as a zero value or the like can be set as the initial value of the operation.

$$\begin{pmatrix} Z_{eff}^{n+1} \\ \sigma_{eff}^{n+1} \end{pmatrix} = \begin{pmatrix} Z_{eff}^{n} \\ \sigma_{eff}^{n} \end{pmatrix} + \begin{pmatrix} \frac{\partial Ac}{\partial Z_{eff}} & \frac{\partial Ac}{\partial \sigma_{eff}^{2}} \\ \frac{\partial Vc}{\partial Z_{eff}} & \frac{\partial Vc}{\partial \sigma_{eff}^{2}} \end{pmatrix}^{-1} \begin{pmatrix} A - Ac^{n} \\ V - Vc^{n} \end{pmatrix} \quad (13)$$

In this step, for the effective atomic number, the material characteristic calculation unit 1203 calculates the effective atomic number based on the rate of change of the pixel average value of the radiation image which is obtained based on the energy spectrum and the attenuation coefficient of the radiation with which the subject is irradiated with respect to the effective atomic number, the rate of change of the pixel average value with respect to the surface density, and the difference between the average value and the pixel average value.

Also, for the surface density, the update processing unit 1402 of the material characteristic calculation unit 1203 calculates the surface density based on the rate of change of the pixel variance value of the radiation image which is obtained based on the energy spectrum of the radiation with which the subject is irradiated and the attenuation coefficient with respect to the effective atomic number, the rate of change of the pixel variance value with respect to the surface density, and the difference between the variance value and the pixel variance value.

The update processing unit 1402 of the material characteristic calculation unit 1203 performs analysis by setting the effective atomic number, which is based on the rate of change of the pixel average value and the difference between the average value and the pixel average value, and the surface density, which is based on the rate of change of the pixel variance value and the difference between the variance value and the pixel variance value, as simultaneous equations and updates the effective atomic number and the surface density by performing an iterative operation based on the result of the analysis.

(Step S1305: Convergence Determination)

In step S1305, the determination unit 1403 of the material characteristic calculation unit 1203 determines the convergence of the effective atomic number and the surface density that have been updated by the update processing unit 1402. The determination unit 1403 determines whether the effective atomic number ($Z_{eff}$) of the material and the surface density ($\sigma_{eff}$) of the material, which have been updated by the iteration calculation performed in step S1304, have converged. Various kinds of methods can be used as the convergence method to make this determination. For example, in a case in which the difference between an nth update operation result and an (n+1)th update operation result is equal to a predetermined threshold or less upon comparing these two update operation results, the determination unit 1403 can determine that the (n+1)th update operation result has converged because predetermined calculation accuracy has been obtained. Alternatively, the iteration count of the update operation by the update processing unit 1402 can be obtained, and the determination unit 1403 can determine that the update operation result has converged when the update operation has been executed for a predetermined iteration count.

If the determination unit 1403 determines that the update operation result has not converged in the convergence determination performed in step S1305 (NO in step S1305), the process returns to step S1303, and the generation processing of integrated values (calculation of the parameters to be used in the arithmetic processing) is executed again. On the other hand, if the determination unit 1403 determines that the update operation result has converged in the convergence determination performed in step S1305 (YES in step S1305), the material characteristic calculation unit 1203 outputs the converged effective atomic number or the converged surface density as the effective atomic number or the surface density of the material forming the subject, and outputs the converged effective atomic number image as the material characteristic image. Through the processing in steps S1301 to S1305, the material characteristic calculation unit 1203 (generation unit) generates, as the material characteristic image, the effective atomic number image in which a region for each material can be extracted from the interior of the subject based on the pixel values of the radiation image and the variance of the pixel values.

The subsequent processing is similar to that from step S302 in the first embodiment. The region enhancement/attenuation unit 111 performs image processing of enhancing or attenuating the radiation image based on the material characteristic image generated by the material characteristic calculation unit 1203. That is, the region enhancement/attenuation unit 111 performs image processing of selectively enhancing or attenuating the radiation image based on the generated material characteristic image.

Eventually, an image in which the region 801 (specific region) in the radiation image 8a in FIG. 8 has been enhanced or attenuated or an image in which a region other than the region 801 (specific region) has been enhanced or attenuated is generated. With this processing, the processing performed in the image processing unit 1209 ends.

According to the processing performed in the image processing unit 1209 of this embodiment, it is possible to obtain an image, such as the radiation image 11a in FIG. 11, in which the radiopaque dye region 1101 (the region corresponding to the region 801 (specific region) in the radiation image 8a in FIG. 8) of the radiation image has been enhanced.

Further, according to the processing performed in the image processing unit 1209 of this embodiment, it is possible to generate a pseudo DSA (Digital Subtraction Angiography) image in which the radiopaque dye region 1102 has been extracted as illustrated in the image 11b in FIG. 11 by attenuating a region other than the radiopaque dye region 1101. In the image 11b in FIG. 11, the image processing unit 109 can generate a more suitable pseudo DSA image by enhancing the radiopaque dye region 1102 while attenuating the region outside the radiopaque dye region.

For example, the gain adjustment unit 212 of the region enhancement/attenuation unit 111 performs gain adjustment by multiplying the region 801 (specific region) in the radiation image 8a in FIG. 8 by a gain that enhances the region 801 (specific region) and multiplying the region other than the region 801 (specific region) by a gain that attenuates a region other than the specific region, and the frequency reconstruction unit 213 reconstructs gain-adjusted radiation images (band limited image HXGn and low-frequency image LXGn). Thus, it is possible to generate a pseudo DSA image in which the radiopaque dye region 1102 has been enhanced while the region other than the radiopaque dye region 1102 has been attenuated.

This embodiment is useful for, even when radiation images having different spectra cannot be obtained, generating a material characteristic image and enhancing or attenuating a predetermined region in a radiation image using the material characteristic image.

Note that the present invention is not limited to the above-described embodiments, and various changes and modifications can be made without departing from the scope of the present invention. The present invention can adopt an embodiment in the form of, for example, a system, apparatus, method, program, or storage medium. More specifically, the present invention may be applied to a system constituted by a plurality of devices, or an apparatus comprising a single device.

According to the present invention, it becomes possible to enhance or attenuate, based on the position of a specific region in a material characteristic image, the specific region in a corresponding radiation image.

Other Embodiments

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus, comprising:
a generation unit configured to generate a material characteristic image regarding a material characteristic of a subject using a plurality of radiation images corresponding to a plurality of radiation energies; and
an image processing unit configured to perform processing of enhancing or attenuating a specific region in a radiation image of the subject using a position of the specific region in the material characteristic image.

2. The information processing apparatus according to claim 1, further comprising a reconstruction unit configured to reconstruct an image in which the specific region has been enhanced or attenuated.

3. The information processing apparatus according to claim 1, wherein the image processing unit is configured to refer to the position of the specific region in the material characteristic image, and to perform image processing of the specific region in the radiation image corresponding to the position of the specific region in the material characteristic image.

4. The information processing apparatus according to claim 1, wherein the image processing unit is configured to refer to the position of the specific region in the material characteristic image, and to perform image processing of another region obtained by excluding the specific region in the radiation image corresponding to the position of the specific region in the material characteristic image.

5. The information processing apparatus according to claim 4, wherein the image processing unit is configured to refer to the position of the specific region in the material characteristic image, and to perform image processing of both the specific region in the radiation image and the other region in the radiation image.

6. The information processing apparatus according to claim 5, wherein the image processing unit is configured to refer to the position of the specific region in the material characteristic image, and to perform image processing of enhancing the specific region in the radiation image or attenuating the region other than the specific region in the radiation image.

7. The information processing apparatus according to claim 1, further comprising a resolution unit configured to resolve each of the radiation image and the material characteristic image into a plurality of band limited images limited to different frequency bands and a low-frequency image, wherein the image processing unit sets, an adjustment coefficient for enhancing or attenuating the specific region in both the band limited image and the low-frequency image of the radiation image based on the position of the specific region in the material characteristic image resolved into the low-frequency image.

8. The information processing apparatus according to claim 7, wherein the image processing unit is configured to set an adjustment coefficient for enhancing or attenuating the region other than the specific region in the radiation image based on the position of the specific region in the material characteristic image resolved into the low-frequency image.

9. The information processing apparatus according to claim 8, wherein the image processing unit is configured to set different adjustment coefficients for the specific region and the region other than the specific region.

10. The information processing apparatus according to claim 7, wherein the image processing unit is configured to set different adjustment coefficients for the specific region in the band limited image and the specific region in the low-frequency image of the radiation image.

11. The information processing apparatus according to claim 1, wherein the material characteristic image includes an effective atomic number image indicating a distribution of an effective atomic number of a material forming the subject or a material decomposition image in which a material forming the subject has been decomposed.

12. The information processing apparatus according to claim 1, wherein the image processing unit is configured to perform the processing of enhancing or attenuating a specific region in a band limited image obtained by the radiation image using a position of the specific region in a low-frequency image obtained by the material characteristic image.

13. An information processing apparatus, comprising:
a generation unit configured to generate a material characteristic image regarding a material characteristic of a subject using pixel values of a radiation image of the subject and a variance of the pixel values; and
an image processing unit configured to perform processing of enhancing or attenuating a specific region in the radiation image using a position of the specific region in the material characteristic image.

14. The information processing apparatus according to claim 13, further comprising:
an average value obtainment unit configured to obtain an average value of pixel values of a radiation image obtained by capturing the subject; and
a variance value obtainment unit configured to obtain a variance value of the pixel values of the radiation image, wherein
the generation unit is configured to generate an effective atomic number image indicating a distribution of an effective atomic number of a material forming the subject as the material characteristic image, and
the generation unit is configured to calculate an effective atomic number or a surface density of the material forming the subject based on the average value and the variance value.

15. The information processing apparatus according to claim 14, wherein the generation unit is configured to calculate the effective atomic number based on a rate of change of a pixel average value of a radiation image which is obtained based on an energy spectrum and an attenuation coefficient of radiation with which the subject is irradiated with respect to the effective atomic number, a rate of change of the pixel average value with respect to the surface density, and a difference between the average value and the pixel average value.

16. The information processing apparatus according to claim 15, wherein the generation unit is configured to calculate the surface density based on a rate of change of a pixel variance value of a radiation image which is obtained based on the energy spectrum of the radiation with which the subject is irradiated and the attenuation coefficient with respect to the effective atomic number, a rate of change of the pixel variance value with respect to the surface density, and a difference between the variance value and the pixel variance value.

17. The information processing apparatus according to claim 16, wherein the generation unit is configured to obtain the rate of change of the pixel average value or the rate of change of the pixel variance value by generating interpolation information for interpolating the attenuation coefficient using the energy of the radiation, an atomic number of an already known element, and an attenuation coefficient corresponding to the atomic number.

18. The information processing apparatus according to claim 17, wherein the generation unit is configured to obtain the rate of change of the pixel average value or the rate of change of the pixel variance value by obtaining a rate of change per unit atomic number of the attenuation coefficient that has been interpolated based on the interpolation information.

19. The information processing apparatus according to claim 17, wherein the generation unit is configured to analyze as simultaneous equations (i) the effective atomic number obtained based on the rate of change of the pixel average value and the difference between the average value and the pixel average value, and (ii) the surface density obtained based on the rate of change of the pixel variance value and the difference between the variance value and the pixel variance value, and updates the effective atomic number and the surface density by performing an iterative operation based on a result of the analysis.

20. The information processing apparatus according to claim 19, further comprising:
a determination unit configured to determine convergence of the effective atomic number and the surface density that have been updated, wherein
the generation unit is configured to output the effective atomic number or the surface density that has converged as the effective atomic number or the surface density of the material forming the subject.

21. The information processing apparatus according to claim 13, wherein the image processing unit is configured to perform the processing of enhancing or attenuating a specific region in a band limited image obtained by the radiation image using a position of the specific region in a low-frequency image obtained by the material characteristic image.

22. An information processing apparatus, comprising:
a generation unit configured to generate an effective atomic number image or a material decomposition image of a subject using a plurality of radiation images corresponding to a plurality of radiation energies; and
an image processing unit configured to perform processing of enhancing or attenuating a specific region in a band limited image obtained by a radiation image of the subject using a position of the specific region in a low-frequency image obtained by the effective atomic number image or the material decomposition image.

23. An information processing apparatus, comprising:
a generation unit configured to generate an effective atomic number image of the subject using pixel values of a radiation image of a subject and a variance of the pixel values; and
an image processing unit configured to perform processing of enhancing or attenuating a specific region in a band limited image obtained by a radiation image of the subject using a position of the specific region in a low-frequency image obtained by the effective atomic number image.

24. A method of processing information based on a radiation image capturing a subject, the method comprising the steps of:
generating a material characteristic image regarding a material characteristic of the subject based on a plurality of radiation images corresponding to a plurality of radiation energies; and
performing processing of enhancing or attenuating a specific region in the radiation image based on a position of the specific region in the material characteristic image.

25. A non-transitory storage medium storing a program for causing a computer to execute each step of the information processing method defined in claim 24.

26. A method of processing information based on a radiation image capturing a subject, the method comprising the steps of:
generating a material characteristic image regarding a material characteristic of the subject using pixel values of the radiation image and a variance of the pixel values; and
performing processing of enhancing or attenuating a specific region in the radiation image based on a position of the specific region in the material characteristic image.

27. A non-transitory storage medium storing a program for causing a computer to execute each step of the information processing method defined in claim 26.

28. A radiation imaging apparatus that comprises a capturing unit configured to capture a radiation image of an object, and which is configured to process information based on a radiation image that has captured a subject by the capturing unit, comprising:
a generation unit configured to generate a material characteristic image regarding a material characteristic of the subject using a plurality of radiation images corresponding to a plurality of radiation energies; and
an image processing unit configured to perform processing of enhancing or attenuating the specific region in the radiation image using a position of a specific region in the material characteristic image.

29. A radiation imaging apparatus that comprises a capturing unit configured to capture a radiation image, and which is configured to process information based on a radiation image that has captured a subject by the capturing unit, comprising:
a generation unit configured to generate a material characteristic image regarding a material characteristic of the subject using pixel values of the radiation image and a variance of the pixel values; and
an image processing unit configured to perform processing of enhancing or attenuating a specific region in the radiation image using a position of the specific region in the material characteristic image.

* * * * *